United States Patent [19]
de Reinach Hirtzbach et al.

[11] Patent Number: 4,493,729
[45] Date of Patent: Jan. 15, 1985

[54] N-PHENYLCARBAMOYL-PYRIDINE COMPOUNDS

[75] Inventors: Francois de Reinach Hirtzbach, Lyons; Dominique Ambrosi, Charbonnieres les Bains, both of France

[73] Assignee: Rhone-Poulenc Agrochimie, Lyons, France

[21] Appl. No.: 283,136

[22] Filed: Jul. 14, 1981

[30] Foreign Application Priority Data

Jul. 16, 1980 [FR] France ............... 80 15993
Jul. 16, 1980 [FR] France ............... 80 15994

[51] Int. Cl.³ .................. C07D 211/90; C07D 213; C07D 56; A01N 43/40
[52] U.S. Cl. .......................... 71/94; 546/316
[58] Field of Search ................. 546/316; 71/94

[56] References Cited
FOREIGN PATENT DOCUMENTS 0003105  7/1979  European Pat. Off. ......... 546/316
2248028  5/1975  France ........................ 546/321
52-33676 3/1977  Japan .
0077955  5/1955  Netherlands ................. 546/316

Primary Examiner—Alan L. Rotman
Attorney, Agent, or Firm—Burns, Doane, Swecker & Mathis

[57] ABSTRACT

Aniline derivatives of the general formula:

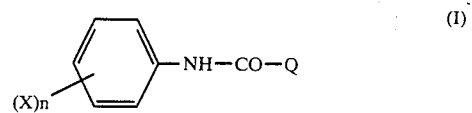

wherein X represents a halogen atom or a lower alkyl, lower alkoxy, lower alkenyl, lower alkenyloxy, lower alkyl substituted by one or more halogen atoms, nitro or cyano group or an amino group unsubstituted or substituted by one or two lower alkyl groups, which may be the same or different, or by a group $-CO-R^1$ (wherein $R^1$ represents a lower alkyl, lower alkoxy, mono (lower) alkylamino group or di (lower) alkylamino group wherein the lower alkyl groups may be the same or different), n represents 0 or an integer from 1 to 5 inclusive, it being understood that when n represents an integer from 2 to 5 inclusive, atoms or groups represented by X may be the same or different, and Q represents a group of the general formula:

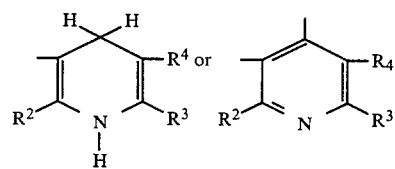

wherein $R^2$ and $R^3$ may be the same or different and each represents a hydrogen atom or a lower alkyl group, and $R^4$ represents a cyano group or a group $-COR^5$, wherein $R^5$ represents a hydroxy or $OR^6$ group, wherein $R^6$ represents a lower alkyl group and, when $R^5$ represents a hydroxy group, agriculturally-acceptable inorganic and organic salt thereof, and, when Q represents a group of general formula IIB, wherein $R^2$, $R^3$ and $R^4$ are as hereinbefore defined, agriculturally acceptable acid addition salts thereof possess useful herbicidal properties.

15 Claims, No Drawings

N-PHENYLCARBAMOYL-PYRIDINE COMPOUNDS

DESCRIPTION

This invention relates to new aniline derivatives, to processes for their preparation, herbicidal compositions which contain them and their use in the selective control of weeds in crops, more especially cotton and sunflower.

Certain 1,4-dihydro-3-(N-phenylcarbamoyl)pyridine derivatives have already been described in the literature; French Patent Application No. 2,248,028 describes the compound of the formula:

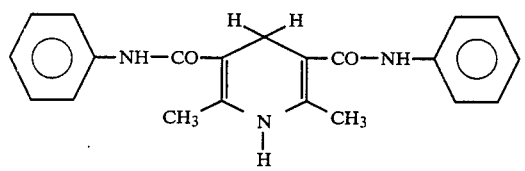

as a medicament. This compound does not, however, exhibit the necessary level of activity for use as a herbicide in agriculture.

Certain N-phenylcarbamoyl-pyridine derivatives have already been described in the literature. Published European Patent Application No. 00/03,105 describes a process for the preparation of carboxyanilides, including 2,6-dimethyl-3,5-dicarboxanilide-pyridine. Certain of the carboxyanilides are stated to be useful plant-protection products. 2,6-Dimethyl-3,5-dicarboxanilide-pyridine does not, however, exhibit a sufficient level of activity for use as a herbicide in agriculture.

The present invention relates to new aniline derivatives of the general formula:

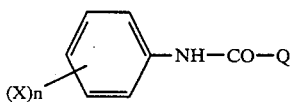

wherein X represents a halogen atom or a lower alkyl, lower alkoxy, lower alkenyl, lower alkenyloxy, lower alkyl substituted by one or more halogen atoms, nitro or cyano group or an amino group unsubstituted or substituted by one or two lower alkyl groups, which may be the same or different, or by a group —CO—$R^1$ (wherein $R^1$ represents a lower alkyl, lower alkoxy, mono (lower) alkylamino group or di (lower) alkylamino group wherein the lower alkyl groups may be the same or different), n represents 0 or an integer from 1 to 5 inclusive, it being understood that when n represents an integer from 2 to 5 inclusive, atoms or groups represented by X may be the same or different, and Q represents a group of the general formula:

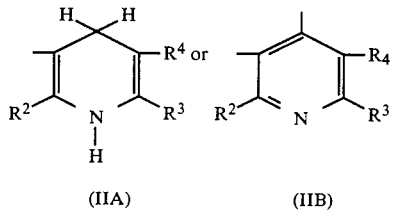

wherein $R^2$ and $R^3$ may be the same or different and each represents a hydrogen atom or a lower alkyl group, and $R^4$ represents a cyano group or a group —CO$R^5$, wherein $R^5$ represents a hydroxy or O$R^6$ group, wherein $R^6$ represents a lower alkyl group and, when $R^5$ represents a hydroxy group, agriculturally-acceptable inorganic and organic salts thereof, for example sodium and potassium salts and primary, secondary and tertiary amine salts, e.g. mono-, di- and trialkanolamine salts and, when Q represents a group of general formula IIB, wherein $R^2$, $R^3$ and $R^4$ are as hereinbefore defined, agriculturally-acceptable acid addition salts thereof.

It is to be understood that the term "lower" as applied in the present specification and the accompanying claims to alkyl, alkoxy, alkenyl and alkenyloxy groups within the definitions of the symbols X, $R^1$, $R^2$, $R^3$, $R^4$ and $R^6$, and the alkyl moieties of mono- and dialkylamino groups within the definition of the symbol $R^1$, contain not more than six carbon atoms and may be straight- or branched-chain.

In this specification and the accompanying claims it is to be understood that references to salts of compounds of general formula I are to inorganic and organic salts of compounds of general formula I in which $R^4$ represents a group —CO$R^5$ wherein $R^5$ represents a hydroxy group; references to acid addition salts of compounds of general formula I are to acid addition salts of compounds of general formula I wherein Q represents a group of general formula IIB.

Preferred compounds of general formula I according to the present invention are those wherein X represents a halogen atom, a straight- or branched-chain alkyl group containing from 1 to 4 carbon atoms, a straight- or branched-chain alkoxy group containing from 1 to 4 carbon atoms, a straight- or branched-chain alkenyl group containing from 3 to 5 carbon atoms or a straight- or branched-chain alkyl group containing from 1 to 4 carbon atoms and substituted by one or more halogen atoms, e.g. trifluoromethyl, or represents a cyano group, $R^2$ and $R^3$, which may be the same or different, each represent a hydrogen atom or a straight- or branched-chain alkyl group containing from 1 to 3 carbon atoms, $R^4$ represents an alkoxycarbonyl group containing from 2 to 6 carbon atoms or a cyano group, n represents 0, 1, 2, 3 or 4, atoms or groups represented by the symbol X being the same or different when n represents 2, 3 or 4.

More especially preferred compounds of general formula I according to the present invention are those of the general formula:

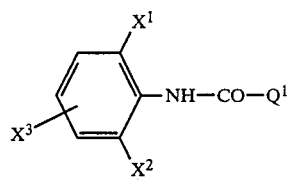

wherein $X^1$ represents a straight- or branched-chain alkyl group containing from 1 to 3 carbon atoms, preferably methyl or ethyl, $X^2$ represents a hydrogen atom or a straight- or branched-chain alkyl group containing from 1 to 3 carbon atoms, preferably methyl or ethyl, $X^3$ represents a hydrogen atom or a halogen, preferably chlorine, atom or a straight- or branched-chain alkyl group containing from 1 to 3 carbon atoms and $Q^1$ represents a group of the general formula:

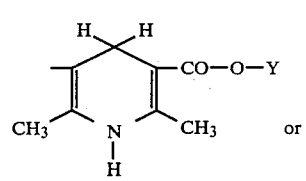 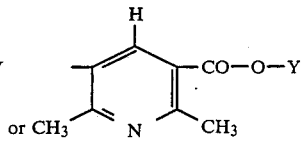

(IVA)    (IVB)

wherein Y represents a straight- or branched-chain alkyl group containing from 1 to 4 carbon atoms.

The compounds of general formula I wherein Q represents a group of formula IIA may exist in tautomeric form and the present invention includes such tautomers.

Preferred compounds of general formula I wherein Q represents a group of general formula IIA are 1,4-dihydro-3-[N-(2,6-diethylphenyl)-carbamoyl]-5-ethoxycarbonyl-2,6-lutidine, 1,4-dihydro-3-[N-(2,6-dimethylphenyl)-carbamoyl]-5-ethoxycarbonyl-2,6-lutidine, 1,4-dihydro-3-[N-(2,6-diethylphenyl)-carbamoyl]-5-methoxycarbonyl-2,6-lutidine, 1,4-dihydro-3-[N-(2-ethyl-6-methylphenyl)-carbamoyl]-5-ethoxycarbonyl-2,6-lutidine and 1,4-dihydro-3-[N-(3-chloro-2,6-dimethylphenyl)-carbamoyl]-5-methoxycarbonyl-2,6-lutidine. These compounds are described as compounds Nos. 1,3,14, 4 and 20, respectively, in the Examples hereinafter.

Preferred compounds of general formula I wherein Q represents a group of general formula IIB are 2,6-dimethyl-3-[N-(2,6-dimethylphenyl)-carbamoyl]-5-ethoxycarbonyl-pyridine, 2,6-dimethyl-3-[N-(2,6-diethylphenyl)-carbamoyl]-5-ethoxycarbonyl-pyridine and 2,6-dimethyl-3-[N-(3-chloro-2,6-dimethylphenyl)-carbamoyl]-5-ethoxy-carbonyl-pyridine. These compounds are described as compounds Nos. 33, 24 and 44, respectively, in the Examples hereinafter.

According to a feature of the present invention the compounds of general formula I may be prepared by the reaction of an anilide of the general formula:

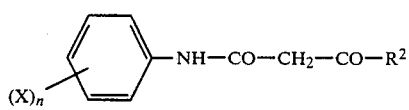

with formaldehyde and an ethylenic amine of the general formula:

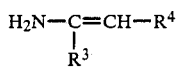

(wherein X, n, $R^2$, $R^3$ and $R^4$ are as hereinbefore defined), to give a compound of general formula I wherein Q represents a group of formula IIA (wherein X, n, $R^2$, $R^3$ and $R^4$ are as hereinbefore defined), according to the reaction scheme:

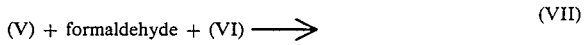

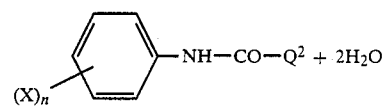

wherein X and n are as hereinbefore defined and $Q^2$ represents a group of formula IIA wherein $R^2$, $R^3$ and $R^4$ are as hereinbefore defined, followed, if desired, by the dehydrogenation of the group $Q^2$ of a compound of general formula VII (wherein X, n and $Q^2$ are as hereinbefore defined) to give a compound of the general formula:

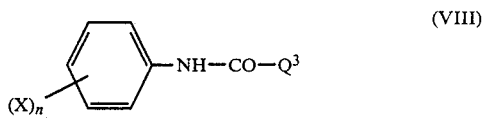

wherein X and n are as hereinbefore defined and $Q^3$ represents a group of formula IIB, wherein $R^2$, $R^3$ and $R^4$ are as hereinbefore defined.

The preparation of compounds of general formula VII wherein X, n and $Q^2$ are as hereinbefore defined, i.e. the compounds of general formula I, wherein X and n are as hereinbefore defined and Q represents a group of formula IIA, wherein $R^2$, $R^3$ and $R^4$ are as hereinbefore defined, by the reaction together of compounds of general formula V, formaldehyde and VI, wherein the various symbols are as hereinbefore defined, and the preparation of compounds of general formula VIII, wherein X, n and $Q^3$ are as hereinbefore defined, i.e. the compounds of general formula I, wherein X and n are as hereinbefore defined and Q represents a group of formula IIB, wherein $R^2$, $R^3$ and $R^4$ are as hereinbefore defined, each form features of the present invention.

The reaction of the anilide of general formula V, formaldehyde and the ethylenic amine of general formula VI is exothermic. It is generally carried out in an organic solvent medium at or above ambient temperature. When the reaction is carried out at a temperature higher than ambient temperature it is to be understood that this temperature must remain below the thermal degradation temperature of the starting reactants and the products formed. Temperatures between 15° C. and 100° C. generally give good results.

Suitable solvents for the reaction of the anilide, formaldehyde and the ethylenic amine include customary protic or aprotic organic solvents, such as aromatic hydrocarbons, aliphatic or cycloaliphatic hydrocarbons, halogenohydrocarbons, lower alkanols, e.g. methanol, ethanol, isopropanol and tert.-butyl alcohol, ethers, e.g. diethyl ether, nitriles, e.g. acetonitrile, and amides, such as dimethylformamide. Advantageously, the reaction is carried out in an organic solvent at the reflux temperature of the reaction mixture. If necessary, the reaction can be carried out in a closed vessel or under an inert gas atmosphere, e.g. a nitrogen atmosphere.

The reaction takes place as soon as the three reactants of formulae V and VI and formaldehyde are brought into contact; it is advantageously carried out by dissolving the anilide of formula V and the ethylenic amine of formula VI in a suitable solvent and then adding formaldehyde to the solution thus obtained.

The compound of general formula I wherein Q represents a group IIA can be separated from the reaction mixture by known methods; generally, it crystallises from the reaction mixture after cooling or the addition of water. It can then be purified by known methods such as recrystallisation from a suitable solvent or liquid phase chromatography.

By the expression known methods as used in this specification is meant methods heretofore used or described in the chemical literature.

The dehydrogenation of the group $Q^2$ of a compound of general formula VII (wherein X, n and $Q^2$ are as hereinbefore defined) to give a compound of general formula VIII wherein X, n and $Q^3$ are as hereinbefore defined, can be carried out by known methods, in particular by the methods described in Chemical Reviews 1972, Volume 72, No. 1, page 31, for example:

by reaction with an oxidising agent such as nitrous acid (generally formed in situ by reacting sodium nitrite with acetic acid), nitric acid, chromic acid, iodine or sulphur, or by heating the dihydropyridine of general formula VII, if necessary in the presence of a dehydrogenation catalyst e.g. palladium.

In the case of some of the compounds of general formula VII which have been prepared, it has also been observed that the dehydrogenation of the dihydropyridine to give the corresponding pyridine sometimes takes place spontaneously at or above ambient temperature, in the absence of a catalyst, after a longer or shorter period of time.

Advantageously, the conversion of the dihydropyridine of general formula VII to the pyridine of general formula VIII is carried out by reacting sodium nitrite with suspension of the dihydropyridine of general formula VII in acetic acid. As the reaction is exothermic, it is generally preferred to cool the reaction mixture so that its temperature does not exceed 25° C.

The pyridine of general formula VIII is separated from the reaction mixture by known methods. Generally, the reaction mixture is neutralised with an inorganic base and the pyridine is precipitated. The pyridine of general formula VIII can then be purified by known methods such as recrystallisation from a suitable solvent (e.g. ethanol) or liquid phase chromatography.

The ethylenic amines of general formula VI used as starting materials are commercially available. The anilides of general formula V can be prepared from appropriate starting materials by the method described in "Organic Syntheses" Volume 3, page 10.

The aniline derivatives of general formula I wherein $R^4$ in the group of general formula IIA or IIB represents a group —$COR^5$, in which $R^5$ represents a hydroxy group, may be converted by known methods into agriculturally-acceptable inorganic and organic salts thereof. The aniline derivatives of general formula I wherein Q represents a group of general formula IIB may be converted by known methods into agriculturally acceptable acid addition salts thereof, for example hydrochlorides.

The following Examples 1 to 5 illustrate the preparation of compounds according to the present invention. The structure of the compounds prepared was confirmed by infra-red spectrometry and/or by nuclear magnetic resonance spectrometry (NMR), the NMR spectra having been run at 60 megahertz in DMSO, with hexamethyldisiloxane as the internal reference.

EXAMPLE 1

Preparation of 1,4-dihydro-3-[N-(2,6-diethylphenyl)-carbamoyl]-5-ethoxycarbonyl-2,6-lutidine (compound No. 1) of the formula:

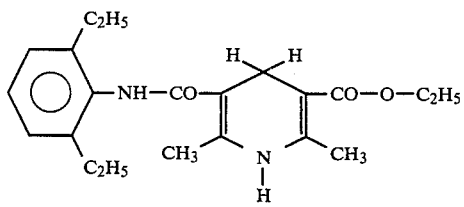

2,6-Diethylacetoacetanilide (23.3 g; 0.1 mol), ethyl β-aminocrotonate (12.9 g; 0.1 mol) and ethanol (50 ml) are introduced into a 250 ml three-necked round-bottomed flask fitted with a condenser, a thermometer and a central mechanical stirrer.

The mixture is stirred and then heated from ambient temperature to 35° C. and kept at this temperature until the reactants have completely dissolved.

After cooling to 20° C., a 30% w/w aqueous solution of formaldehyde (10 ml, i.e. about 0.1 mol) is run into the mixture in the course of one minute. The reaction is exothermic and the temperature rises spontaneously from 20° C. to about 55° C. The reaction mixture is then heated under reflux for 60 minutes.

After cooling to ambient temperature, filtering off the precipitate obtained and washing it with water, a mixture (14.5 g) is obtained which comprises both the desired product (compound No. 1) and, as a by-product, 1,4-dihydro-3,5-di-(ethoxycarbonyl)-2,6-lutidine, the formation of which results from the condensation of two mols of ethyl β-aminocrotonate and one mol of formaldehyde.

Compound No. 1 (9 g) is obtained by recrystallisation from ethanol (250 ml). Yield relative to the starting acetoacetanilide: 25%. M.p.: 209° C. Empirical formula: $C_{21}H_{28}N_2O_3$.

The starting 2,6-diethylacetoacetanilide was prepared by reacting 2,6-diethylaniline with diketen in accordance with the method described in "Organic Syntheses, Volume 3, page 10" for the preparation of acetoacetanilide.

EXAMPLE 2

Preparation of compounds Nos. 2 to 22.

By following the method described in the preceding example, compounds Nos. 2 to 22 were prepared from the appropriate starting materials. The formulae and physicochemical characteristics of these compounds are indicated in Table A hereinafter.

EXAMPLE 3

Preparation of compound No. 23.

By following the method described in Example 1, 1,4-dihydro-3-[N-(2,6-diethylphenyl)-carbamoyl]-5-cyano-2,6-lutidine was prepared from the appropriate starting materials.

M.p.=200° C.

Empirical formula: $C_{19}H_{23}N_3O$.

EXAMPLE 4

Preparation of 3-[N-(2,6-diethylphenyl)-carbamoyl]-5-ethoxycarbonyl-2,6-lutidine (compound No. 24), or, according to another equivalent name, 2,6-dimethyl-3-[N-(2,6-diethylphenyl)-carbamoyl]-5-ethoxycarbonyl-pyridine, of the formula

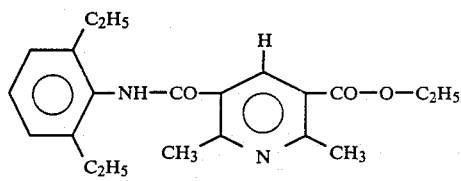

1,4-Dihydro-3-[N-(2,6-diethylphenyl)-carbamoyl]-5-ethoxycarbonyl-2,6-lutidine (5.5 g), prepared as described in Example 1, and acetic acid (55 ml) are introduced into a 250 ml three-necked round-bottomed flask fitted with a condenser, a thermometer and a central mechanical stirrer.

The reaction mixture is cooled to 16° C. and sodium nitrite (1.2 g) is then added in small portions. The exothermic reaction is controlled by cooling with the aid of an ice-bath, so that the temperature of the reaction mixture does not exceed 25° C. After stirring for 30 minutes at about 20°-25° C., the reaction mixture is poured onto ice and neutralised with concentrated aqueous ammonia solution (75 ml). The precipitate obtained is filtered off and washed with water. After filtration on silica (120 g) and elution with an 8/2 mixture of methylene chloride/diethyl ether, the desired compound (compound No. 24) (4.2 g) is obtained:

m.p.: 216° C.

yield (from the dihydrolutidine): 77%;

empirical formula: $C_{21}H_{26}N_2O_3$.

EXAMPLE 5

Preparation of compounds Nos. 25 to 54.

By following the procedure described in Examples 1 and 4 compounds Nos. 25 to 53 were prepared from the appropriate starting materials. Compound No. 54 was prepared by following the procedure of Example 4 but using as starting material 1,4-dihydro-3-[N-(2,6-dimethylphenyl)-carbamoyl]-5-cyano-2,6-lutidine, itself prepared by the procedure of Example 1, using appropriate starting materials. The formulae and physicochemical characteristics of these compounds are indicated in Table B hereinafter. The yields indicated in this Table are calculated relative to the starting acetoacetanilide.

The following Example 6 illustrates the herbicidal activity of the compounds of the invention.

EXAMPLE 6

Herbicidal activity, in a greenhouse, in the pre-emergence treatment of plant species.

A number of seeds are sown in 9×9×9 cm pots filled with light agricultural earth, this number being determined as a function of the plant species and the size of the seed. The seeds are then covered with an approximately 3 mm thick layer of earth. After moistening the earth, the pots are treated by spraying each pot with an amount of spraying mixture which corresponds to a volume of 500 liters/ha and contains the active ingredient at the relevant dose.

The spraying mixture was prepared by adding an amount of water sufficient to give the desired concentration to a wettable powder having the following composition by weight:

active ingredient to be tested: 20% solid inert carrier: kaolinite: 69% surface-active agent (deflocculant): calcium lignosulphonate: 5% surface-active agent (wetting agent): sodium isopropyl-naphthalenesulphonate: 1% anti-caking silica: 5%

This powder was obtained by mixing and grinding the ingredients in a microniser so as to give an average particle size of less than 40 microns.

Depending on the concentration of active ingredient in the spraying mixture, the dose of active ingredient applied was equivalent to 2 to 8 kg/ha.

The treated pots are then placed in troughs which are intended to receive the moistening water, by sub-irrigation, and are kept for 35 days at ambient temperature and at 70% relative humidity.

After 35 days, the number of living plants in the pots treated with the spraying mixture containing the active ingredient to be tested, and the number of living plants in a control pot treated under the same conditions, but with a spraying mixture not containing active ingredient, are counted. The percentage destruction of the treated plants, relative to the untreated control, is thus determined. A percentage destruction of 100% indicates that there has been complete destruction of the plant species in question, and a percentage of 0% indicates that the number of living plants in the treated pots is identical to that in the control pot.

For this experiment, the plant species used were as follows:

| Adventitious | Symbol used |
| --- | --- |
| wild oat (Avena fatua) | WO |
| finger grass (Digitaria sanguinalis) | FIN |
| panic grass (Echinochloa crus-galli) | PAN |
| ray grass (Lolium multiflorum) | RAY |
| foxtail grass (Setaria faberii) | FOX |
| slender foxtail (Alopecurus myosuroides) | SF |
| goosefoot (Chenopodium sp.) | GOO |
| black night-shade (Solanum nigrum) | BN |
| wild mustard (Sinapis arvensis) | WM |
| chickweed (Stellaria media) | CHI |
| Crops | |
| cotton (Gossypium barbadense) | COT |
| sunflower (Helianthus annuus) | SUN |

The results obtained are indicated in Table C hereinafter.

These results show the excellent herbicidal activity of the compounds according to the invention on the majority of the adventitious plants treated, both graminaceous plants and dicotyledon plants, and also their selectivity with respect to the crops in question.

For their use in practice, the compounds according to the invention are rarely employed by themselves, but are most frequently employed in the form of compositions which also constitute a feature of the invention. The herbicidal compositions according to the invention comprise, as active ingredient, a compound of general formula I, wherein X, n and Q are as hereinbefore defined, or an agriculturally acceptable salt or acid addition salt thereof, in association with an inert carrier which is acceptable in agriculture and/or a surface active agent which is acceptable in agriculture.

In the present specification, the term "carrier" denotes a natural or synthetic, organic or inorganic material with which the active ingredient may be associated in order to facilitate its application to the plants or to the soil. The carrier can be solid (e.g. clays, natural or synthetic silicates, silica, resins, waxes and solid fertilisers) or liquid (e.g. water, alcohols, petroleum fractions, aromatic or paraffinic hydrocarbons, chlorohydrocarbons and liquefied gases).

The surface-active agent may be an emulsifying, dispersing, deflocculating or wetting agent of the ionic or non-ionic type. Examples which may be mentioned are salts of polyacrylic acids, salts of lignosulphonic acids, salts of phenolsulphonic or naphthalenesulphonic acids, polycondensates of ethylene oxide with fatty alcohols, fatty acids or fatty amines, substituted phenols (especially alkylphenols or arylphenols), salts of sulphosuccinic acid esters, taurine derivatives (especially alkyltaurines), and phosphoric acid esters of condensates of ethylene oxide with alcohols or phenols.

The compositions according to the invention usually contain from 0.001% to about 95% (by weight) of one or more compounds according to the invention. The proportion of surface-active agent therein is generally from 0 to 20% by weight.

However, the compositions can also contain other ingredients, e.g. thickeners, thixotropic agents, protective colloids, adhesives, penetrating agents and stabilisers, and also other known active ingredients having pesticidal properties (especially herbicidal, fungicidal and insecticidal properties) or properties for assisting plant growth (especially fertilisers) or properties for regulating plant growth. More generally, the compounds according to the invention may be associated with any solid or liquid additives by the customary techniques for the preparation of pesticidal compositions.

The compositions according to the invention can be prepared in the form of, for example, wettable powders, dusting powders, granules, solutions, emulsifiable concentrates, emulsions, suspension concentrates and aerosols.

The wettable powders or spraying powders usually contain from 20 to 95% by weight of active ingredient and generally contain, in addition to a solid carrier, from 0 to 5% by weight of wetting agent and from 3 to 10% by weight of one or more stabilisers and/or other additives, such as penetrating agents, adhesives or anti-caking agents and dyestuffs.

They are prepared by mixing the constituents in mixers and grinding them in mills or other suitable grinders, for example air grinders, to obtain the desired particle size.

The following Examples 7 to 9 illustrate herbicidal compositions according to the invention. In these Examples percentages are by weight. The compositions of Examples 7, 8 and 9 are wettable powders.

EXAMPLE 7 active ingredient (compound No. 1): 80%
sodium alkylnaphthalenesulphonate: 2%
sodium lignosulphonate: 2%
anti-caking silica: 3%
kaolinite: 13%

EXAMPLE 8 active ingredient (compound No. 3): 50%
sodium alkylnaphthalenesulphonate: 2%
low-viscosity methylcellulose: 2%
diatomaceous earth: 46%

EXAMPLE 9 active ingredient (compound No. 14): 90%
sodium dioctylsulphosuccinate: 0.2%
synthetic silica: 9.8%

The active ingredients in Examples 7, 8 and 9 may be replaced by any other compound according to the invention; for example compound No. 24.

Granular compositions, which are intended to be placed on the soil, are usually prepared so that the granules have dimensions of between 0.1 and 2 mm, and they can be manufactured by agglomeration or impregnation. In general, the granules will contain from 0.5 to 25% by weight of active ingredient and from 0 to 10% by weight of additives, such as stabilisers, slow-release modifiers, binders and solvents.

Emulsifiable concentrates, which can be applied by spraying, usually contain from 10 to 50% by weight/volume of active ingredient. In addition to the active ingredient and the solvent, they can also contain, if necessary, from 2 to 20% by weight/volume of suitable additives, such as surface-active agents, stabilisers, penetrating agents, corrosion inhibitors, dyestuffs and adhesives.

Suspension concentrates, which can also be applied by spraying, are prepared so as to give a stable fluid product which does not form a deposit, and they usually contain from 10 to 75% by weight of active ingredient, from 0.5 to 15% by weight of surface-active agents, from 0.1 to 10% by weight of thixotropic agents, from 0 to 10% of suitable additives, such as anti-foam agents, corrosion inhibitors, stabilisers, penetrating agents and adhesives, and, as a carrier, water or an organic liquid in which the active ingredient is substantially insoluble: certain organic solids, or inorganic salts, can be dissolved in the carrier in order to assist in preventing sedimentation or to act as anti-freeze agents for the water.

The aqueous dispersions and emulsions, which are obtained by diluting the abovementioned compositions with water, especially the wettable powders and emulsifiable concentrates according to the invention, are also included in the general scope of the present invention. The emulsions thus obtained can be of the water-in-oil type or of the oil-in-water type and they can have a thick consistency such as that of a mayonnaise.

All these aqueous dispersions and emulsions, or spraying mixtures, can be applied by any suitable means to the crops in which weeds are to be destroyed, generally by spraying, at doses which are generally of the order of 500 to 1,000 liters of spraying mixture per hectare.

As indicated above, the invention also relates to a method for destroying weeds in crops, such as cotton and sunflower crops, in accordance with which an effective amount of at least one of the compounds according to the invention is applied to the plants and/or to the soil in the area in which weeds are to be destroyed.

The present invention accordingly provides a method for the control of the growth of weeds at a locus which comprises applying to the locus a compound of general formula I, or an agriculturally acceptable salt or acid addition salt thereof, or a herbicidal composition according to the invention.

Generally, amounts of active ingredient ranging from 0.5 to 10 kg/ha give good results, it being understood that the choice of the amount of active ingredient to be used depends on the severity of the weed problem, the climatic conditions and the crop in question. The treatment is generally carried out as a pre-emergence treatment of the crops and adventitious plants or as a pre-sowing treatment of the crops, with incorporation into the soil, although in certain cases, depending on the compound used, good results can also be obtained by post-emergence treatment.

TABLE A

General structure: (X)$_n$-phenyl-NH-CO-C(=C(CH$_3$)-NH-C(CH$_3$)=C-CO-O-R$_5$ (1,4-dihydropyridine core with CH at 4-position)

| Compound No. | (X)$_n$-phenyl substituent | R$_5$ | Empirical formula | M.p. (°C.) | Yield % |
|---|---|---|---|---|---|
| 2 | 2-CH$_3$ phenyl | C$_2$H$_5$ | C$_{18}$H$_{22}$N$_2$O$_3$ | 164 | 29 |
| 3 | 2,6-(CH$_3$)$_2$ phenyl | C$_2$H$_5$ | C$_{19}$H$_{24}$N$_2$O$_3$ | 159 | 20 |
| 4 | 2-C$_2$H$_5$,6-CH$_3$ phenyl | C$_2$H$_5$ | C$_{20}$H$_{26}$N$_2$O$_3$ | 163 | 32 |
| 5 | 2-Cl phenyl | C$_2$H$_5$ | C$_{17}$H$_{19}$ClN$_2$O$_3$ | 100 | 30 |
| 6 | 2-Cl phenyl | CH$_3$ | C$_{16}$H$_{17}$ClN$_2$O$_3$ | 125 | 67 |
| 7 | 3-Cl phenyl | C$_2$H$_5$ | C$_{17}$H$_{19}$ClN$_2$O$_3$ | 190 | 26 |
| 8 | 2,3-Cl$_2$ phenyl | C$_2$H$_5$ | C$_{17}$H$_{18}$Cl$_2$N$_2$O$_3$ | 136 | 30 |
| 9 | phenyl | —C$_2$H$_5$ | C$_{17}$H$_{20}$N$_2$O$_3$ | 142 | 19 |

TABLE A-continued

[Structure: (X)n-phenyl-NH-CO-[3,5-dihydro-2,6-dimethylpyridine]-CO-O-R5]

| Compound No. | (X)n (phenyl) | R5 | Empirical formula | M.p. (°C.) | Yield % |
|---|---|---|---|---|---|
| 10 | 2,4-(CH$_3$)$_2$ | —C$_2$H$_5$ | C$_{19}$H$_{24}$N$_2$O$_3$ | 175 | 21 |
| 11 | 2,5-(CH$_3$)$_2$ | —C$_2$H$_5$ | C$_{19}$H$_{24}$N$_2$O$_3$ | 165 | 17 |
| 12 | 2-CF$_3$ | —C$_2$H$_5$ | C$_{18}$H$_{19}$F$_3$N$_2$O$_3$ | 145 | 25 |
| 13 | 2-CN | —C$_2$H$_5$ | C$_{18}$H$_{19}$N$_3$O$_3$ | 136 | 47 |
| 14 | 2,6-(C$_2$H$_5$)$_2$ | —CH$_3$ | C$_{20}$H$_{26}$N$_2$O$_3$ | 211 | 18 |
| 15 | 2,4,6-(CH$_3$)$_3$ | —C$_2$H$_5$ | C$_{20}$H$_{26}$N$_2$O$_3$ | 165 | 33 |
| 16 | 3-CH$_3$ | —C$_2$H$_5$ | C$_{18}$H$_{22}$N$_2$O$_3$ | 140 | 26 |
| 17 | 2-OC$_2$H$_5$ | —C$_2$H$_5$ | C$_{19}$H$_{24}$N$_2$O$_4$ | 117 | 31 |

TABLE A-continued

[Structure: (X)n-phenyl-NH-CO-C=C(CH3)-NH-C(CH3)=C-CO-O-R5, with H,H at 4-position of dihydropyridine]

| Compound No. | (X)n-phenyl | R5 | Empirical formula | M.p. (°C.) | Yield % |
|---|---|---|---|---|---|
| 18 | 2-CH3, 3-C2H5 | —CH3 | $C_{19}H_{24}N_2O_3$ | 184 | 38 |
| 19 | 2-CH3, 3-CH3, 4-F (2,3-dimethyl-4-fluorophenyl) | —C2H5 | $C_{18}H_{21}FN_2O_3$ | 148 | 27 |
| 20 | 2-Cl, 3-CH3, 5-CH3 | —CH3 | $C_{18}H_{21}ClN_2O_3$ | 175 | 30 |
| 21 | 2-C2H5, 3-C2H5 | —(CH2)2—CH3 | $C_{22}H_{30}N_2O_3$ | 180–185 | 89 |
| 22 | 2-CH3, 4-CH3 | —C2H5 | $C_{19}H_{24}N_2O_3$ | 166 | 70 |

TABLE B

[Structure: (X)n-phenyl-NH-CO-C=C(CH3)-N=C(CH3)-C(COOC2H5)=C-H (pyridine)]

| Compound No | (X)n-phenyl | Empirical formula | M.p. (°C.) | Yield % |
|---|---|---|---|---|
| 25 | phenyl | $C_{17}H_{18}N_2O_3$ | 105 | 11 |

TABLE B-continued
| | | | | |
|---|---|---|---|---|
| 26 | 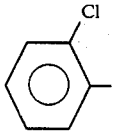 2-Cl-phenyl | C$_{17}$H$_{17}$ClN$_2$O$_3$ | 136 | 40 |
| 27 | 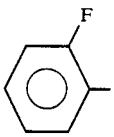 2-F-phenyl | C$_{17}$H$_{17}$FN$_2$O$_3$ | 137 | — |
| 28 | 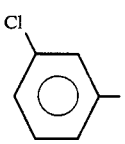 3-Cl-phenyl | C$_{17}$H$_{17}$ClN$_2$O$_3$ | 88 | 23 |
| 29 | 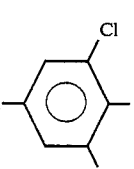 2,4,5-triCl-phenyl | C$_{17}$H$_{15}$Cl$_3$N$_2$O$_3$ | 189 | 51 |
| 30 | 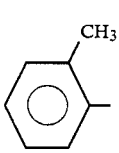 2-CH$_3$-phenyl | C$_{18}$H$_{20}$N$_2$O$_3$ | 132 | 12 |
| 31 | 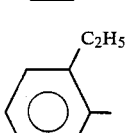 2-C$_2$H$_5$-phenyl | C$_{19}$H$_{22}$N$_2$O$_3$ | 188 | 4 |
| 32 | 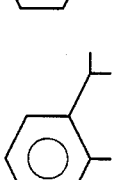 2-iPr-phenyl | C$_{20}$H$_{24}$N$_2$O$_3$ | 133 | — |
| 33 | 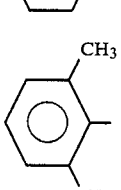 2,4-diCH$_3$-phenyl | C$_{19}$H$_{22}$N$_2$O$_3$ | 187 | 17 |
| 34 | 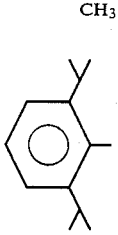 2,6-diiPr-phenyl | C$_{23}$H$_{30}$N$_2$O$_3$ | 159 | — |
| 35 | 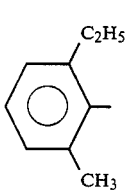 2-C$_2$H$_5$-4-CH$_3$-phenyl | C$_{20}$H$_{24}$N$_2$O$_3$ | 203 | 19 |

TABLE B-continued
| | | Empirical formula | M.p. (°C.) | Yield % |
|---|---|---|---|---|
| 36 | 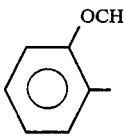 OCH₃ | $C_{18}H_{20}N_2O_4$ | 86 | — |
| 37 | 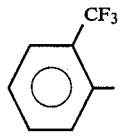 CF₃ | $C_{18}H_{17}F_3N_2O_3$ | 175 | 18.5 |
| 38 | 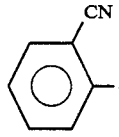 CN | $C_{18}H_{16}Cl_2N_2O_3$ | 174 | 23.5 |
| 39 | 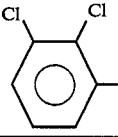 Cl, Cl | $C_{17}H_{16}Cl_2N_2O_3$ | 162 | 15 |
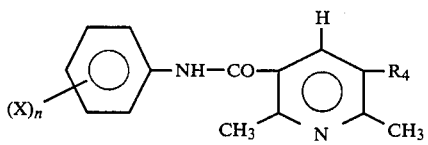
| Compound No. | $(X)_n$ 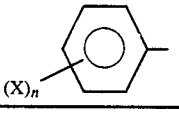 | $R_4$ | Empirical formula | M.p. (°C.) | Yield % |
|---|---|---|---|---|---|
| 40 | 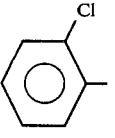 Cl | —COO—CH₃ | $C_{16}H_{15}ClN_2O_3$ | 142 | 49 |
| 41 | 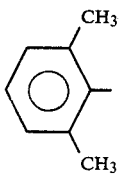 CH₃, CH₃ | —CN | $C_{17}H_{17}N_3O$ | 243 | 65 |
| 42 | 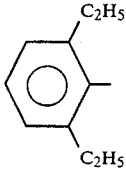 C₂H₅, C₂H₅ | —COOCH₃ | $C_{20}H_{24}N_2O_3$ | 192 | 25 |
| 43 | 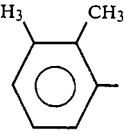 CH₃, CH₃ | —COOC₂H₅ | $C_{19}H_{22}N_2O_3$ | 185 | 12 |

TABLE B-continued

| # | Aryl | R | Formula | mp | yield |
|---|---|---|---|---|---|
| 44 | 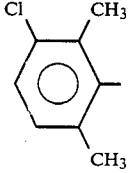 1-Cl, 2-CH₃, 4-CH₃ phenyl | —COOC$_2$H$_5$ | C$_{19}$H$_{21}$ClN$_2$O$_3$ | 205 | 15 |
| 45 | 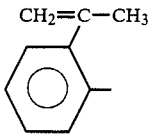 2-(CH$_2$=C—CH$_3$) phenyl | —COOC$_2$H$_5$ | C$_{20}$H$_{22}$N$_2$O$_3$ | 116 | 10 |
| 46 | 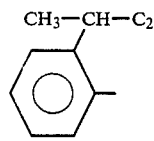 2-(CH$_3$—CH—C$_2$H$_5$) phenyl | —COOC$_2$H$_5$ | C$_{21}$H$_{26}$N$_2$O$_3$ | 95–96 | 20 |
| 47 | 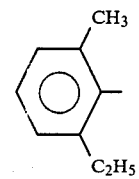 2-CH$_3$, 6-C$_2$H$_5$ phenyl | —COOCH$_3$ | C$_{19}$H$_{22}$N$_2$O$_3$ | 188 | 34 |
| 48 | 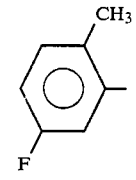 2-CH$_3$, 6-CH$_3$, 4-F phenyl | —COOC$_2$H$_5$ | C$_{18}$H$_{19}$FN$_2$O$_3$ | 156 | 25 |
| 49 | 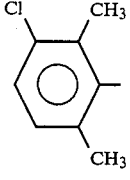 1-Cl, 2-CH$_3$, 6-CH$_3$ phenyl | —COOCH$_3$ | C$_{18}$H$_{19}$ClN$_2$O$_3$ | 207 | 30 |
| 50 | 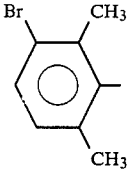 1-Br, 2-CH$_3$, 6-CH$_3$ phenyl | —COOC$_2$H$_5$ | C$_{19}$H$_{21}$BrN$_2$O$_3$ | 208 | 14 |
| 51 | 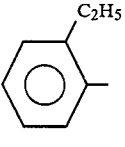 2-C$_2$H$_5$ phenyl | —COOC$_2$H$_5$ | C$_{19}$H$_{22}$N$_2$O$_3$ | 188 | 20 |
| 52 | 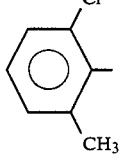 2-Cl, 6-CH$_3$ phenyl | —COOC$_2$H$_5$ | C$_{18}$H$_{19}$ClN$_2$O$_3$ | 178 | 21 |

TABLE B-continued

| | | | | | |
|---|---|---|---|---|---|
| 53 | 2-C(CH₃)₃, 6-CH₃ phenyl | —COOC₂H₅ | $C_{21}H_{26}N_2O_3$ | 70 | 50 |
| 54 | 2,3,6-tri-CH₃ phenyl | CN | $C_{17}H_{17}N_3O$ | 243 | |

TABLE C

Herbicidal activity in a pre-emergence treatment:
100 = complete destruction
0 = no herbicidal action

| Compound No. | Dose kg/ha | ADVENTITIOUS PLANTS | | | | | | | | | | CROPS | |
|---|---|---|---|---|---|---|---|---|---|---|---|---|---|
| | | WO | FIN | PAN | RAY | FOX | SF | GOO | BN | WM | CHI | COT | SUN |
| 1 | 2 | 30 | 100 | 80 | 80 | 100 | 100 | 100 | 100 | 15 | 100 | 0 | 0 |
| | 4 | 90 | 100 | 100 | 80 | 100 | 100 | 100 | 100 | 50 | 100 | 0 | 0 |
| | 8 | 90 | 100 | 100 | 100 | 100 | 100 | 100 | 100 | 95 | 100 | — | 0 |
| 2 | 4 | 20 | 100 | 80 | 30 | 100 | 100 | 90 | 100 | 50 | 60 | 0 | 15 |
| 3 | 4 | 50 | 100 | 80 | 20 | 100 | 30 | 100 | 100 | 100 | 100 | 0 | 0 |
| 4 | 4 | 60 | 100 | 100 | 100 | 80 | 90 | 100 | 100 | 95 | 100 | 0 | 0 |
| | 8 | 60 | 100 | 100 | 100 | 90 | 100 | 100 | 100 | 100 | 100 | 0 | 20 |
| 5 | 8 | 40 | — | 40 | 30 | — | — | 100 | — | 30 | — | — | — |
| 6 | 8 | 90 | 100 | 0 | 80 | 100 | 100 | 100 | 100 | 30 | 100 | 0 | 0 |
| 7 | 8 | 70 | — | 30 | 10 | — | — | 100 | — | 30 | — | — | — |
| 8 | 4 | 20 | 90 | 30 | 40 | 100 | 100 | 100 | 100 | 20 | 100 | 0 | 0 |
| 9 | 8 | 60 | — | 30 | 20 | — | — | 100 | — | 30 | — | — | — |
| 10 | 8 | 10 | — | 75 | 0 | — | — | 80 | — | 20 | — | — | — |
| 11 | 8 | 40 | — | 100 | 90 | — | — | 100 | — | 100 | — | — | — |
| 12 | 8 | 20 | — | 30 | 30 | — | — | 100 | — | 50 | — | — | — |
| 13 | 8 | 10 | — | 75 | 20 | — | — | 90 | — | 0 | — | — | — |
| 14 | 2 | 5 | 100 | 80 | 90 | 100 | 100 | 100 | 100 | 100 | 100 | 10 | 0 |
| 15 | 8 | 80 | — | 100 | 90 | — | — | 100 | — | 100 | — | — | — |
| 16 | 8 | 50 | — | 80 | 60 | — | — | 100 | — | 100 | — | — | — |
| 17 | 8 | 80 | — | 95 | 95 | — | — | 100 | — | 20 | — | — | — |
| 18 | 8 | 100 | — | 100 | 100 | — | — | 100 | — | 100 | — | — | — |
| 19 | 8 | 40 | — | 95 | 90 | — | — | 100 | — | 100 | — | — | — |
| 20 | 8 | 100 | — | 100 | 100 | — | — | 100 | — | 100 | — | — | — |
| 22 | 8 | 30 | 95 | 100 | 90 | 100 | 95 | 100 | 100 | 60 | 100 | — | — |
| 23 | 8 | 90 | — | 100 | 95 | — | — | 100 | — | 100 | — | — | — |
| 25 | 8 | 10 | 90 | 50 | 5 | 100 | 20 | 100 | 100 | 30 | 0 | 0 | 0 |
| 26 | 8 | 50 | 100 | 50 | 20 | 100 | 80 | 100 | 100 | 30 | 15 | — | — |
| 27 | 4 | 5 | 80 | 30 | 10 | 100 | 20 | 80 | 100 | 10 | 5 | 0 | 0 |
| | 8 | 20 | 100 | 50 | 20 | 100 | 40 | 100 | 100 | 50 | 5 | 0 | — |
| 28 | 8 | 0 | 50 | 20 | 5 | 100 | 15 | 100 | 100 | 5 | 80 | 0 | — |
| 29 | 8 | 0 | — | 0 | 0 | — | — | 100 | — | 20 | — | — | — |
| 30 | 4 | 5 | 100 | 20 | 50 | 100 | 80 | 70 | 100 | 30 | 20 | — | 0 |
| | 8 | 50 | 100 | 70 | 60 | 100 | 100 | 95 | 100 | 40 | 40 | — | — |
| 31 | 8 | 50 | — | 90 | 70 | — | — | 100 | — | 80 | — | — | — |
| 32 | 8 | 10 | — | 75 | 30 | — | — | 100 | — | 60 | — | — | — |
| 33 | 2 | 5 | 100 | 50 | 10 | 100 | 20 | 100 | 100 | 25 | 95 | 0 | 0 |
| | 4 | 50 | 100 | 50 | 50 | 100 | 20 | 100 | 100 | 95 | 100 | 0 | — |
| | 8 | 80 | 100 | 80 | 50 | 100 | 70 | 100 | 100 | 95 | 100 | 0 | — |
| 34 | 8 | 0 | — | 0 | 0 | — | — | 80 | — | 30 | — | — | — |
| 35 | 4 | 0 | 100 | 40 | 30 | 30 | 100 | 60 | 100 | 60 | 100 | 0 | 0 |
| 36 | 8 | 0 | — | 20 | 20 | — | — | 60 | — | 50 | — | — | — |
| 37 | 8 | 0 | 20 | 40 | 0 | 60 | 0 | 90 | 100 | 0 | 50 | 0 | 0 |
| 38 | 8 | 50 | — | 80 | 50 | — | — | 90 | 20 | — | — | — | — |
| 39 | 8 | 0 | 20 | 20 | 0 | 95 | 20 | 90 | 100 | 0 | 100 | 0 | 0 |
| 40 | 8 | 90 | — | 30 | 80 | — | — | 30 | — | 60 | — | — | — |
| 41 | 8 | 90 | — | 30 | 30 | — | — | 100 | — | 100 | — | — | — |
| 42 | 2 | 0 | 100 | 60 | 80 | 100 | 90 | 100 | 100 | 60 | 100 | 0 | 0 |
| | 4 | 60 | 100 | 95 | 95 | 100 | 100 | 100 | 100 | 80 | 100 | 0 | 0 |
| 43 | 8 | 90 | — | 100 | 60 | — | — | 100 | — | 100 | — | — | — |
| 44 | 8 | 95 | — | 100 | 100 | — | — | 100 | — | 100 | — | — | — |
| 45 | 8 | 20 | — | 20 | 20 | — | — | 100 | — | 20 | — | — | — |
| 46 | 8 | 20 | — | 30 | 20 | — | — | 100 | — | 100 | — | — | — |
| 47 | 8 | 100 | — | 100 | 100 | — | — | 100 | — | 100 | — | — | — |
| 48 | 8 | 90 | — | 100 | 100 | — | — | 100 | — | 100 | — | — | — |
| 49 | 8 | 98 | — | 100 | 100 | — | — | 100 | — | 100 | — | — | — |
| 50 | 8 | 30 | — | 98 | 80 | — | — | 100 | — | 100 | — | — | — |

TABLE C-continued

Herbicidal activity in a pre-emergence treatment:
100 = complete destruction
0 = no herbicidal action

| Compound No. | Dose kg/ha | ADVENTITIOUS PLANTS | | | | | | | | | | CROPS | |
|---|---|---|---|---|---|---|---|---|---|---|---|---|---|
| | | WO | FIN | PAN | RAY | FOX | SF | GOO | BN | WM | CHI | COT | SUN |
| 51 | 8 | 5 | 100 | 60 | 20 | 100 | 60 | 100 | 100 | 20 | 100 | 0 | 0 |
| 52 | 8 | 0 | 98 | 90 | 10 | 100 | 30 | 100 | 100 | 80 | 95 | 0 | 0 |
| 53 | 8 | 0 | 95 | 0 | 0 | 95 | 20 | 100 | 100 | 0 | 100 | 0 | 0 |
| 54 | 8 | 5 | 98 | 20 | 10 | 100 | 5 | 100 | 100 | 20 | 0 | 0 | 0 |

We claim:

1. N-phenylcarbamoyl pyridine derivatives of the general formula:

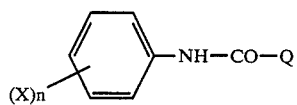

wherein X represents a halogen atom or a lower alkyl, lower alkoxy, lower alkenyl, lower alkenyloxy, lower alkyl substituted by one or more halogen atoms, nitro or an amino group unsubstituted or substituted by one or two lower alkyl groups, which may be the same or different, or by a group —CO—$R^1$ (wherein $R^1$ represents a lower alkyl, lower alkoxy, mono(lower)alkylamino group or di(lower)alkylamino group wherein the lower alkyl groups may be the same or different), n represents an integer from 1 to 5 inclusive, it being understood that when n represents an integer from 2 to 5 inclusive, atoms or groups represented by X may be the same or different, and Q represents a group of the general formula:

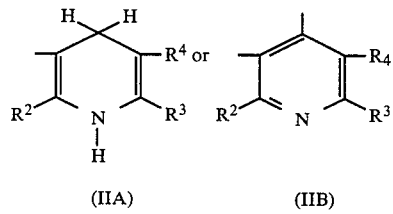

wherein $R^2$ and $R^3$ may be the same or different and each represents a hydrogen atom or a lower alkyl group, and $R^4$ represents a group —$COR^5$, wherein $R^5$ represents a hydroxy or $OR^6$ group, wherein $R^6$ represents a lower alkyl group and, when $R^5$ represents a hydroxy group, agriculturally-acceptable inorganic and organic salts thereof, and when Q represents a group of general formula IIB, wherein $R^2$, $R^3$ and $R^4$ are as hereinbefore defined, agriculturally acceptable acid addition salts thereof.

2. Compounds according to claim 1, wherein X represents a halogen atom, a straight- or branched-chain alkyl group containing from 1 to 4 carbon atoms, a straight- or branched-chain alkoxy group containing from 1 to 4 carbon atoms, a straight- or branched-chain alkenyl group containing from 3 to 5 carbon atoms or a straight- or branched-chain alkyl group containing from 1 to 4 carbon atoms and substituted by one or more halogen atoms, $R^2$ and $R^3$, which may be the same or different, each represent a hydrogen atom or a straight- or branched-chain alkyl group containing from 1 to 3 carbon atoms, $R^4$ represents an alkoxycarbonyl group containing from 2 to 6 carbon atoms, n represents 1, 2, 3, or 4, atoms or groups represented by the symbol X being the same or different when n represents 2, 3, or 4.

3. Compound according to claim 1 which conform to the general formula:

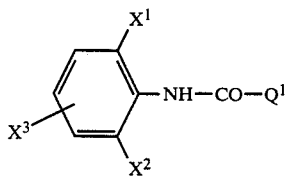

wherein $X^1$ represents a straight- or branched-chain alkyl group containing from 1 to 3 carbon atoms, preferably methyl or ethyl, $X^2$ represents a hydrogen atom or a straight- or branched-chain alkyl group containing from 1 to 3 carbon atoms, preferably methyl or ethyl, $X^3$ represents a hydrogen atom or a halogen, preferably chlorine, atom or a straight- or branched-chain alkyl group containing from 1 to 3 carbon atoms and $Q^1$ represents a group of the general formula:

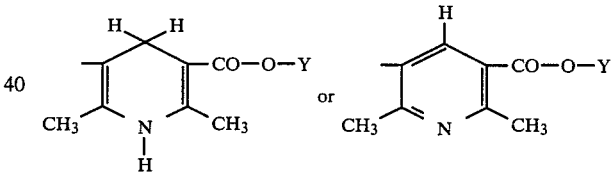

wherein Y represents a straight- or branched-chain alkyl group containing from 1 to 4 carbon atoms.

4. Compound according to claim 3 wherein this compound is selected from amongst the following compounds:

1,4-Dihydro-3-[N-(2,6-diethylphenyl)-carbamoyl]-5-ethoxycarbonyl-2,6-lutidine, 1,4-Dihydro-3-[N-(2,6-dimethylphenyl)-carbamoyl]-5-ethoxycarbonyl-2,6-lutidine, 1,4-Dihydro-3-[N-(2,6-diethylphenyl)-carbamoyl]-5-methoxycarbonyl-2,6-lutidine, 1,4-Dihydro-3-[N-(2-ethyl-6-methylphenyl)-carbamoyl]-5-ethoxycarbonyl-2,6-lutidine, 1,4-Dihydro-3-[N-(3-chloro-2,6-dimethylphenyl)-carbamoyl]-5-methoxycarbonyl-2,6-lutidine, 2,6-Dimethyl-3-[N-(2,6-dimethylphenyl)-carbamoyl]-5-ethoxycarbonyl-pyridine, 2,6-Dimethyl-3-[N-(2,6-diethylphenyl)-carbamoyl]-5-ethoxycarbonyl-pyridine, and 2,6-Dimethyl-3-[N-(3-chloro-2,6-dimethylphenyl)-carbamoyl]-5-ethoxycarbonyl-pyridine.

5. A herbicidal composition which comprises as active ingredient a compound according to claims 1, 2, 3, or 4.

6. A herbicidal composition according to claim 5 which comprises from 0.001% to 95% by weight of active ingredient, in association with an inert carrier which is acceptable in agriculture and/or a surface active agent which is acceptable in agriculture.

7. A method for the control of the growth of weeds at a locus which comprises applying to the locus an effective amount of a compound according to claims 1, 2, 3, or 4, or an agriculturally acceptable salt or acid addition salt thereof.

8. The compound according to claim 4 which is 1,4-dihydro-3-[N-(2,6-diethylphenyl)carbamoyl]-5-ethoxycarbonyl-2,6-lutidine.

9. A herbicidal composition which comprises, as an active ingredient, the compound of claim 8.

10. A herbicidal composition according to claim 9 which comprises from 0.001% to 95% by weight of 1,4-dihydro-3-[N-(2,6-diethylphenyl)carbamoyl]-5-ethoxycarbonyl-2,6-lutidine, in association with an inert carrier which is acceptable in agriculture and/or a surface active agent which is acceptable in agriculture.

11. A method for the control of the growth of weeds at a locus which comprises applying to the locus an effective amount of a compound according to claim 8.

12. A N-phenylcarbamoyl pyridine derivative selected from amongst the following compounds:

1,4-Dihydro-3-[N-(2,6-diethylphenyl)-carbamoyl]-5-ethoxycarbonyl-2,6-lutidine,
1,4-Dihydro-3-[N-(2,6-dimethylphenyl)-carbamoyl]-5-ethoxycarbonyl-2,6-lutidine,
1,4-Dihydro-3-[N-(2,6-diethylphenyl)-carbamoyl]-5-methoxycarbonyl-2,6-lutidine,
1,4-Dihydro-3-[N-(2-ethyl-6-methylphenyl)-carbamoyl]-5-ethoxycarbonyl-2,6-lutidine,
1,4-Dihydro-3-[N-(3-chloro-2,6-dimethylphenyl)-carbamoyl]-5p-methoxycarbonyl-2,6-lutidine,
2,6-Dimethyl-3-[N-(2,6-dimethylphenyl)-carbamoyl]-5-ethoxycarbonyl-pyridine,
2,6-Dimethyl-3-[N-(2,6-diethylphenyl)-carbamoyl]-5-ethoxycarbonyl-pyridine, and
2,6-Dimethyl-3-[N-(3-chloro-2,6-dimethylphenyl)-carbamoyl]-5-ethoxycarbonyl-pyridine.

13. A herbicidal composition which comprises as an active ingredient a compound according to claim 12.

14. A herbicidal composition according to claim 13 which comprises from 0.001% to 95% by weight of active ingredient, in association with an inert carrier which is acceptable in agriculture and/or a surface active agent which is acceptable in agriculture.

15. A method for the control of the growth of weeds at a locus which comprises applying to the locus an effective amount of a compound according to claim 12, or an agriculturally acceptable salt or acid addition salt thereof.

* * * * *